United States Patent [19]

Le Blanc et al.

[11] Patent Number: 4,628,097

[45] Date of Patent: Dec. 9, 1986

[54] PROCESS FOR THE PREPARATION OF 2-AMINO-ALKYLPYRIDINES

[75] Inventors: Helmut Le Blanc; Lothar Puppe, both of Burscheid; Karlfried Wedemeyer, Cologne, all of Fed. Rep. of Germany

[73] Assignee: Bayer Aktiengesellschaft, Leverkusen, Fed. Rep. of Germany

[21] Appl. No.: 645,947

[22] Filed: Aug. 30, 1984

[30] Foreign Application Priority Data

Sep. 10, 1983 [DE] Fed. Rep. of Germany ....... 3332687

[51] Int. Cl.$^4$ .................. C07D 213/73; C07D 213/09
[52] U.S. Cl. ...................................... 546/251; 546/250
[58] Field of Search ................................ 546/250, 251

[56] References Cited

U.S. PATENT DOCUMENTS 2,892,841  6/1959  Rudner ................................ 546/143
3,702,886  11/1972 Argauer et al. ..................... 423/328
3,860,650  1/1975  Becker et al. ....................... 564/330
4,388,461  6/1983  Chang et al. ........................ 546/251
4,395,554  7/1983  Chang et al. ........................ 546/250

FOREIGN PATENT DOCUMENTS 0062542  10/1982  European Pat. Off. ............ 564/305
0082613  6/1983   European Pat. Off. ............ 546/251
2032403   1/1971   Fed. Rep. of Germany ...... 546/251

OTHER PUBLICATIONS

Orchin et al., "The Vocabulary of Organic Chemistry" pp. 557–558, Wiley–Interscience Pub. QD 291C55 1980. Abstract, J5 4095–576, Pharmaceuticals, Week B36, p. 7, J. Med. Phar. Chem., 5, 1063–1065, (1962).

*Primary Examiner*—Alan L. Rotman
*Attorney, Agent, or Firm*—Sprung, Horn, Kramer & Woods

[57] ABSTRACT

2-Amino-alkylpyridines are prepared by catalysed isomerisation of 1,3-diaminobenzenes at elevated temperature.

3 Claims, No Drawings

PROCESS FOR THE PREPARATION OF 2-AMINO-ALKYLPYRIDINES

2-Amino-6-alkylpyridines can be prepared by the Tschitschibabin method by reaction of α-substituted pyridines with sodium amide in inert solvents. Because sodium amide is used, care should be taken that water is excluded completely when this process is carried out. However, this requires a considerable expenditure on safety measures. A further disadvantage of the reaction is that the sodium hydride formed must also be destroyed under inert conditions, which is associated with additional costs.

According to Japanese Patent Application No. 54/95 576 (1979), 2-amino-6-methylpyridine is obtained by reacting α-picoline with ammonia in the presence of cobalt-containing catalysts. However, only very moderate yields of 2-amino-6-methylpyridine are obtained in this reaction.

It is known from U.S. Pat. No. 2,892,841 that 2-amino-6-methylpyridine can be prepared from α-picoline and chloramine. The disadvantages of this reaction are the use of chloramine, which tends to decompose and is therefore difficult to handle, and the isolation of the α-amino-α'-picoline in a multi-stage, cumbersome process.

The preparation of α-amino-pyridines by reaction of the corresponding hydroxy compounds with ammonia is furthermore known from German Offenlegungsschrift 2,032,403. In the case of 2-amino-6-methylpyridine, the amination step proceeds with only a 27% yield; in addition, α-alkyl-α'-hydroxypyridines, which are used as starting substances, are not readily accessible.

U.S. Pat. No. 4,388,461 discloses the reaction of ammonia and phenol over ZSM-5 zeolites at 510° C., to give, besides aniline, minor amounts of α-picoline. In addition, a relatively large number of by-products occur, such as toluidines, xylidines and diphenylamine, the formation of which is evidently to be attributed to the very high reaction temperature. This reaction temperature is associated with a high industrial expenditure and probably leads to coking and frequent change or regeneration of the catalyst.

It is furthermore known from European patent specification No. 0,082,613 that aniline can be rearranged to α-picoline over ZSM-5 zeolites at 510° C. Even at aniline conversions of only 8.3 to 27.7%, selectivities of only 32.6–56.6% are achieved for α-picoline. In addition, other nitrogen-containing compounds, such as toluidines, xylidines, diphenylamine, indoles and quinolines, are formed in abundance. Besides the poor conversion and the low yield of the desired substance, major separation problems also arise here.

A process has now been found for the preparation of 2-amino-alkylpyridines of the general formula

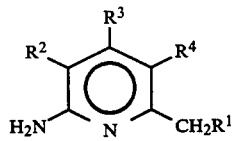

wherein
$R^1$ to $R^4$ are identical or different and represent hydrogen, alkyl, cycloalkyl, aralkyl or aryl,
which is characterized in that 1,3-diaminobenzenes of the general formula

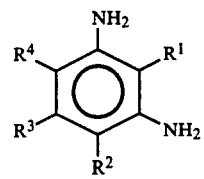

wherein
$R^1$ to $R^4$ have the abovementioned meaning, or the corresponding resorcinol, substituted resorcinol, m-aminophenol or substituted m-aminophenol,
are isomerized catalytically at elevated temperature.

Alkyl radicals which may be mentioned are those with 1 to 6 carbon atoms, preferably 1 to 4 carbon atoms, such as the methyl, ethyl, n-propyl, iso-propyl, n-butyl, iso-butyl, tert.-butyl, n-pentyl, iso-pentyl, tert.-pentyl and hexyl radical, preferably the methyl, ethyl, n-propyl and iso-propyl radical.

Cycloalkyl radicals which may be mentioned are those with 3 to 12 carbon atoms, preferably with 6 to 8 carbon atoms, such as the cyclohexyl and methylcyclohexyl radical, preferably the cyclohexyl radical; aralkyl radicals which may be mentioned are those with 7 to 12 carbon atoms, preferably 7 to 9 carbon atoms, such as the benzyl and methylbenzyl radical, preferably the benzyl radical; and aryl radicals which may be mentioned are those with 6 to 12 carbon atoms, preferably 6 to 9 carbon atoms, such as the phenyl, tolyl and trimethylphenyl radical, preferably the phenyl and tolyl radical.

Examples of diaminobenzenes which can be used in the process according to the invention are 1,3-diaminobenzene, 2,6-diaminotoluene, 2,4-diaminotoluene and 3,5-diaminocumene, preferably 1,3-diaminobenzene.

The process according to the invention is in general carried out in a temperature range from about 250° to 500° C., preferably at 300° to 450° C. and particularly preferably at 350° to 400° C. The process according to the invention can be carried out either under normal pressure or under increased pressure, for example under about 10 to 250 bar, preferably 30 to 190 bar.

Acid catalysts are in general used in the process according to the invention. Both proton acids and Lewis acids are suitable. Examples which may be mentioned are: homo- and hetero-polyacids, zeolites, aluminosilicates and aluminum oxides. The isomerisation according to the invention can advantageously be carried out with zeolites, aluminosilicates and/or γ-aluminum oxide. Zeolites having a ZSM-5 structure, such as those described in U.S. Pat. No. 3,702,886, are particularly suitable.

For carrying out the process according to the invention, the appropriate 1,3-diaminobenzene is usually taken up in an inert solvent and/or diluent, such as water, toluene and/or ammonia, preferably in ammonia, an excess of the solvent and/or diluent generally being used. The amount of solvent and/or diluent to be employed in each case is not critical and can vary within wide limits. The amount suitable can easily be determined by preliminary experiments. Usually the solvent and/or the diluent is employed in an excess of about 5 to 120 mol, preferably 10 to 60 mol, per mol of 1,3-diaminobenzene used.

The process according to the invention can be carried out either in the liquid phase or in the gas phase, preferably in the gas phase. An inert gas, such as nitrogen and/or argon, can be metered into the reaction mixture to increase the flow rate.

The reaction according to the invention can be carried out either batchwise or continuously.

To carry out the process according to the invention, for example, a mixture of ammonia and the appropriate 1,3-diaminobenzene is passed over the catalyst under pressure. After leaving the reactor, the reaction mixture is worked up in a manner which is known per se, for example by fractional distillation. The 1,3-diaminobenzene which has not yet reacted can be recycled back to the reaction with virtually no losses.

The process according to the invention can be represented by the following general equation (using the example of 1,3-diaminobenzene):

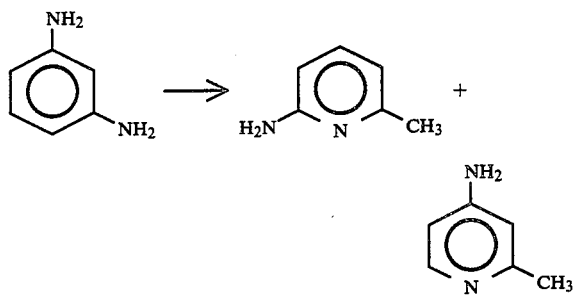

As can be seen from the equation, besides the 2-amino-alkylpyridine, a certain amount of 4-amino-alkylpyridine is always formed in the reaction according to the invention. The amount of 4-amino-alkylpyridine formed depends, inter alia, on the particular reaction conditions used and on the diaminobenzene employed.

In the process according to the invention, it is also possible to use resorcinol or correspondingly substituted resorcinols, or m-aminophenol or correspondingly substituted m-aminophenols instead of the m-phenylenediamines. In this case, it is necessary to carry out the reaction in an ammoniacal medium. The ammonia is employed in an excess of about 2 to 150 mol, preferably 5 to 120 mol and particularly preferably 10 to 60 mol, per mol of resorcinol or aminophenol used. Instead of pure ammonia, it is also possible to use an aqueous-ammoniacal solution, for example a 30% strength aqueous-ammoniacal solution.

The advantages of the process according to the invention are to be seen both in the high selectivity with which the 2-amino-alkylpyridines are formed and in the good yields of 2-amino-alkylpyridines.

The process according to the invention is particularly suitable for the industrial preparation of 2-amino-6-alkylpyridines, because the m-phenylenediamines employed, and in particular 1,3-diaminobenzene, are themselves readily accessible basic organic chemicals which are easy to handle, and the unreacted feed product can easily be distilled off from the end product and can be recycled to the reaction with virtually no losses. A further advantage is that the process according to the invention can be carried out without particular safety measures and, since no effluent is obtained, is particularly non-polluting to the environment.

These advantages are surprising because, according to the prior art, and especially taking into consideration U.S. Pat. No. 4,388,461 and European Pat. No. 82,613, a number of by-products would have been expected, especially since the optionally substituted 1,3-diaminobenzenes to be used according to the invention carry 2 amino groups instead of one. Such by-products could have been, for example, optionally substituted heterocyclic compounds with 2N atoms in the core. The considerably lower reaction temperature in comparison with the rearrangement of aniline, which can also be formed from phenol and NH$_3$, is also surprising. Finally, the high specificity of the reaction is surprising, since the corresponding o- and p-diaminobenzenes do not react in the manner described.

2-Amino-alkylpyridines are used as starting substances for plant protection agents and for pharmaceuticals. For example, 2-amino-6-methylpyridine is an important intermediate for the preparation of pharmaceutical active compounds, such as nalidixic acid (compare J. Med. Pharm. Chem. 5, 1063 (1962)).

The process according to the invention may be illustrated in more detail with the aid of the following examples, without being restricted to these examples.

EXAMPLE 1

A reactor 76 cm in length and 1 cm in diameter and filled with 60 ml of catalyst was heated up to 350° C. in a salt bath. The catalyst was a zeolite with a ZSM-5 structure (compare U.S. Pat. No. 3,702,886). The catalyst had a particle size of 0.5 to 1.0 mm.

A mixture of 12.1 g of ammonia and 1.3 g of 1,3-diaminobenzene per hour (molar ratio 60:1) was vaporised in a pre-evaporator, and the gas mixture, which had been brought to the reaction temperature, was passed through the reactor under a pressure of 190 bar. The mixture was let down and then condensed and subjected to analysis by gas chromatography. The product contained 35.8% of 2-amino-6-methylpyridine, 6.6% of 2-methyl-4-aminopyridine and 56.8% of 1,3-diaminobenzene.

The configuration of the aminopyridines was confirmed by NMR spectroscopy.

Melting points: melting point of 2-amino-6-methylpyridine: 44.5°–45° (literature: 41°); melting point of 2-methyl-4-aminopyridine: 95° (literature: 95°–96°).

EXAMPLE 2

The procedure of Example 1 was repeated, with the modification that a mixture of 11.4 g of ammonia and 1.2 g of 1,3-diaminobenzene (molar ratio 60:1) per hour was passed through the reactor at a temperature of 400° C. The product mixture contained 56.4% of 2-amino-6-methylpyridine, 15.4% of 4-methyl-2-aminopyridine and 26.6% of 1,3-diaminobenzene.

EXAMPLE 3

The procedure of Example 1 was repeated, with the modification that a mixture of 7.4 g of ammonia and 4.7 g of 1,3-diaminobenzene per hour (molar ratio 10:1) was passed through the reactor. The product contained 11.0% of 2-amino-6-methylpyridine, 2.6% of 2-methyl-4-aminopyridine and 86.2% of 1,3-diaminobenzene.

EXAMPLE 4

The procedure of Example 1 was repeated, with the modification that a mixture of 16.3 g of ammonia and 1.7 g of 1,3-diaminobenzene per hour (molar ratio 60:1) was passed through the reactor under a pressure of 30 bar. The product mixture contained 13.1% of 2-amino-6- methylpyridine, 3.8% of 2-methyl-4-aminopyridine and 81.4% of 1,3-diaminobenzene.

EXAMPLE 5

The procedure of Example 1 was repeated, with the modification that a mixture of 12.1 g of ammonia and 1.3 g of 1,3-diaminobenzene per hour (molar ratio 60:1) was passed through the reactor, which was filled with an aluminium silicate (LA-5P from Akzo) containing about 15% of $Al_2O_3$ and 85% of $SiO_2$. The product mixture contained 8.9% of 2-amino-6-methylpyridine, 1.3% of 2-methyl-4-aminopyridine and 84.2% of 1,3-diaminobenzene.

EXAMPLE 6

The procedure of Example 1 was repeated, with the modification that a mixture of 10.1 g of ammonia and 1.1 g of 3-aminophenol (molar ratio 60:1) per hour was passed at a temperature of 400° C. through the reactor, which was filled with highly pure γ-aluminum oxide (D 10—10 from BASF). The product mixture contained 29.1% of 2-amino-6-methylpyridine and 68.4% of 1,3-diaminobenzene.

EXAMPLE 7

The procedure of Example 1 was repeated, with the modification that a mixture of 11.4 g of ammonia and 1.2 g of 3-aminophenol (molar ratio 60:1) per hour was passed at a temperature of 350° C. and under a pressure of 30 bar through the reactor, which was filled with γ-aluminum oxide (D 10—10). The product mixture contained 25.4% of 2-amino-6-methylpyridine and 71.6% of 1,3-diaminobenzene.

EXAMPLE 8

The procedure of Example 1 was repeated, with the modification that a mixture of 11.4 g of ammonia and 1.2 g of resorcinol (molar ratio 60:1) per hour was passed at a temperature of 320° C. through the reactor, which was filled with γ-aluminum oxide (D 10—10). The product mixture contained 15% of 2-amino-6-methylpyridine and 84% of 1,3-diaminobenzene.

EXAMPLE 9

The procedure of Example 1 was repeated, with the modification that a mixture of 11.4 g of ammonia, 1.3 g of water and 1.2 g of 3-aminophenol per hour was passed at a temperature of 380° C. through the reactor, which was filled with highly pure γ-aluminum oxide (BR 1597 from Kali Chemie). The product mixture contained 24.0% of 2-amino-6-methylpyridine and 71.0% of 1,3-diaminobenzene.

EXAMPLE 10

The procedure of Example 1 was repeated, with the modification that a mixture of 3.5 g of ammonia and 0.4 g of 2,6-diaminotoluene (molar ratio 60:1) per hour was passed through the reactor, which was filled with γ-aluminum oxide (D 10—10). The product mixture contained 14.9% of 2-amino-6-methylpyridine and 83.5% of 1,3-diaminobenzene.

EXAMPLE 11

The procedure of Example 1 was repeated, with the modification that a mixture of 3.6 g of ammonia and 0.4 g of 2,4-diaminotoluene (molar ratio 60:1) per hour was passed through the reactor, which was filled with γ-aluminum oxide (D 10—10). The product mixture contained 7.1% of 2-amino-5,6-dimethylpyridine, 11.6% of 2-amino-3,6-dimethylpyridine and 73.5% of 2,4-diaminotoluene.

EXAMPLE 12

The procedure of Example 1 was repeated, with the modification that a mixture of 15.2 g of ammonia and 1.5 g of 3,5-diaminocumene (molar ratio 90:1) per hour was passed through the reactor, which was filled with γ-aluminum oxide (BR 1597). The product mixture contained 10.1% of 2-amino-4-isopropyl-6-methylpyridine and 86.7% of 3,5-diaminocumene. Melting point of 2-amino-4-isopropyl-6-methylpyridine: 59° C.; melting point of 3,5-diaminocumene: 61° C.

EXAMPLE 13

A mixture of 60 g of 1,3-diaminobenzene, 80 g of ammonia and 30 g of zeolite (ZSM-5 powder) was stirred at 350° C. in an 0.7 liter steel autoclave for 12 hours.

The crude product, distilled under a high vacuum (distillate yield: 47.8 g=80% of theory) contained 8.2% of 2-amino-6-methylpyridine, 2.3% of 2-methyl-4-aminopyridine and 88.8% of 1,3-diaminobenzene.

EXAMPLE 14

The procedure of Example 1 was repeated, with the modification that a mixture of 11.5 g of $NH_3$ and 1.2 g of 1,3-diaminobenzene per hour was passed through the reactor at a temperature of 380° C. The resulting product mixture contained 41.1% of 2-amino-6-methylpyridine, 13.6% of 2-methyl-4-aminopyridine and 44.1% of 1,3-diaminobenzene.

EXAMPLE 15 (for comparison)

The procedure of Example 1 was repeated, with the modification that a mixture of 9.9 g of $NH_3$ and 0.9 g of aniline per hour was passed through the reactor at a temperature of 380° C. The resulting product mixture contained 2.9% of α-picoline and 96.7% of aniline.

At 350° C., under otherwise identical conditions, less than 1% of α-picoline was obtained.

What is claimed is:

1. A process for the preparation of a 2-amino-alkyl-pyridine of the formula

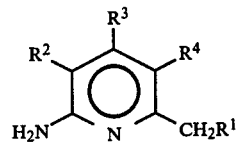

wherein $R^1$ to $R^4$ are identical or different and represent hydrogen, $C_1$ to $C_6$ alkyl, $C_3$ to $C_{12}$ cycloalkyl, aralkyl with 7 to 12 carbon atoms or unsubstituted aryl or aryl substituted by alkyl with 6 to 12 carbon atoms, which comprises heating a reaction mixture consisting essentially of a 1,3-diaminobenzene of the formula

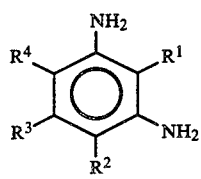

wherein $R^1$ to $R^4$ have the above-mentioned meanings in the presence of ammonia and a catalyst selected from the group consisting of zeolites and gamma-$Al_2O_3$, the process being carried out at a temperature of 250° to 500° C. and at a pressure of 10 to 250 bar.

2. A process according to claim 1 wherein the process is carried out at a temperature of 350° to 450° C. under a pressure of 30 to 190 bar.

3. A process according to claim 1 wherein the catalyst is a zeolite having a ZSM-5 structure.

* * * * *